US00PP31644P2

(12) United States Plant Patent
Zlesak

(10) Patent No.: US PP31,644 P2
(45) Date of Patent: Apr. 14, 2020

(54) POLYANTHA ROSE PLANT NAMED 'ZLEPOLONE'

(50) Latin Name: *Rosa hybrida*
Varietal Denomination: Zlepolone

(71) Applicant: The Conard-Pyle Company, West Grove, PA (US)

(72) Inventor: David Charles Zlesak, River Falls, WI (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/350,688

(22) Filed: Dec. 20, 2018

(51) Int. Cl.
*A01H 5/02* (2018.01)
*A01H 6/74* (2018.01)

(52) U.S. Cl.
USPC ..... Plt./107
CPC ..... *A01H 6/74* (2018.05)

(58) Field of Classification Search
USPC ..... Plt./107
CPC ..... A01H 5/0222
See application file for complete search history.

(56) References Cited

U.S. PATENT DOCUMENTS

PP16,602 P3 5/2006 Lim et al.
PP25,065 P3 11/2014 Radler

OTHER PUBLICATIONS https://rosecatalog.ru/news/29-itogi-konkursa-roz-monaco-2018.html; Sep. 2, 2018; 8 pages.*

* cited by examiner

*Primary Examiner* — Kent L Bell
(74) *Attorney, Agent, or Firm* — Buchanan Ingersoll & Rooney PC

(57) ABSTRACT

A new and distinct variety of polyantha rose plant, herein referred to as 'Zlepolone', is provided which forms abundantly on a substantially continuous basis attractive, double deep purplish pink colored blossoms. Attractive, semi-glossy, medium green foliage is formed, which contrasts beautifully with the blossoms. The vegetation is vigorous and the growth habit is very bushy and compact. The new variety is well suited for providing attractive ornamentation in the landscape.

1 Drawing Sheet

Botanical/commercial classification:
Latin name—*Rosa hybrida.*
Common name—Polyantha Rose Plant.
Varietal denomination: 'Zlepolone'.

SUMMARY OF THE INVENTION

The pollination that led to the new variety of *Rosa hybrida* polyantha rose plant occurred in June of 2007, wherein two parents were crossed which previously had been studied in the hope that they would contribute the desired characteristics. The female parent (i.e., the seed parent) was 'BAlpome' (U.S. Plant Pat. No. 16,602). The male parent (i.e., the pollen parent) was 'Mountain Mignonette' (non-patented).

The parentage of the new variety can be summarized as follows:

'BAlpome' x 'Mountain Mignonette'

The seeds resulting from the above pollination were sown in St. Paul, Minn. and small plants were obtained which were physically and biologically different from each other. Selective study resulted in the identification of a single plant of the new variety.

It was found that the new variety of polyantha rose plant of the present invention possesses the following combination of characteristics:

(a) forms attractive, double deep purplish pink colored blossoms abundantly and substantially continuously, (b) exhibits a very bushy and compact growth habit,
(c) forms vigorous vegetation,
(d) provides attractive ornamental semi-glossy, medium green foliage, and
(e) exhibits excellent disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, 'BAlpome' (i.e., the seed parent) displays single light pink to medium pink colored blooms and exhibits a growth habit that is more spreading and shorter compared to the new variety, whereas the new variety provides double deep purplish pink colored blooms. In addition, 'Mountain Mignonette' (i.e., the pollen parent) displays lavender-pink colored blooms and provides a more rounded and upright plant habit compared to the new variety, whereas the new variety provides deep purplish pink colored blooms. Moreover, the new variety can be readily distinguished from related similar non-parental varieties. For example, 'Radcleome' (U.S. Plant Pat. No. 25,065) displays a less compact growth habit compared to the new variety and provides blooms that are single, whereas the new variety provides blooms that are double.

The new variety has been found to undergo asexual propagation in Cochranville, Pa. by a number of routes, including softwood and semi-hardwood stem cuttings. Asexual propagation by stem cuttings in Cochranville, Pa. has shown that the characteristics of the new variety are stable and are strictly transmissible by such asexual propagation from one generation to another. Accordingly, the new variety undergoes asexual propagation in a true-to-type manner.

The new variety has been named 'Zlepolone'.

BRIEF DESCRIPTION OF THE PHOTOGRAPH

The accompanying photograph of FIG. 1 shows as nearly true as it is reasonably possible to make the same, in a color illustration of this character, a typical specimen of the new variety. The rose plant of the new variety illustrated herein was approximately three years of age and was observed during May of 2018 while growing on its own roots and growing outdoors at Cochranville, Pa., U.S.A.

FIG. 1—illustrates a specimen of the plant with blossoms at varying stages of opening.

DETAILED BOTANICAL DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The description is based on the observation of three-year-old specimens of the new variety during May while growing on their own roots and growing in containers at Cochranville, Pa., U.S.A.

Class: Polyantha Rose Plant.

Plant:

*Habit*.—Very bushy and compact.

*Height*.—Approximately 33.0 cm on average in a three-gallon container.

*Width*.—Approximately 38.0 cm on average in a three-gallon container.

Branches:

*Color*.—Young stems: commonly near Yellow-Green Group 144A. — old wood: commonly near Green Group 137B.

*Length*.—Main stems: approximately 20.0 cm on average. — secondary stems: approximately 8.0 cm on average.

*Diameter*.—Approximately 3.0 mm on average.

*Internode length*.—Approximately 1.7 cm on average.

*Prickles*.—Young prickles: length is approximately 5.0 mm on average, width is approximately 2.0 mm at point of attachment, and color is commonly near Greyed-Orange Group 177D. — old prickles: length is approximately 6.0 mm on average, width is approximately 3.0 mm on average, and color is commonly near Greyed- Orange Group 177D.

Foliage:

*General appearance*.—Medium green with a semi-glossy aspect.

*Number of leaflets*.—3, 5, and 7.

*5-leaflet leaf*.—Length: approximately 6.3 cm on average. — width: approximately 3.5 cm on average.

*Young foliage*.—Upper surface color: commonly near Yellow-Green Group 144A. — under surface color: commonly near Yellow-Green Group 144B.

*Old foliage*.—Upper surface color: commonly near Green Group 138A. — under surface color: commonly near Green Group 138B.

Leaflets:

*Shape*.—Ovate; apex is acute; and base is cuneate.

*Texture*.—Upper and under surface is smooth.

*Terminal leaflet*.—Length: approximately 2.7 cm on average. — width: approximately 1.4 cm on average.

*Lower leaflet*.—Length: approximately 1.5 cm on average. — width: approximately 1.0 cm on average.

*Leaf margin*.—Serrate.

*Petiole*.—Upper and under surfaces: color is commonly near Yellow-Green Group 144A and texture is sparsely glandular and moderately pubescent. — length: approximately 1.0 cm on average. — diameter: approximately 1.0 mm on average.

*Rachis*.—Color of upper and under surfaces: commonly near Yellow-Green Group 144A. — length: approximately 2.5 cm on average. — diameter: approximately 1.0 mm on average.

*Stipules*.—Margin: entire to erose. — length: approximately 13.0 mm on average. — width: approximately 3.0 mm on average. — color of upper and under surfaces: commonly near Green Group 143B.

Inflorescence:

*Number of flowers*.—Generally about 50-60 blooms on average on a plant at once.

*Number of blooms per stem or in a cluster*.—Generally up to 10 blooms per cluster.

*Bud*.—Shape: round. — length: approximately 1.0 cm on average. — width: approximately 6.0 mm on average. — color when opening: commonly between near Red-Purple Group 62A and Red-Purple Group 62B.

*Sepals*.—Number: commonly 5 on average. — length: approximately 1.0 cm on average. — width: approximately near 4.0 mm on average. — shape: lanceolate; apex is aristulate to aristate. — margin: entire with extensions on two or three sepals measuring approximately 3.0 mm in length on average and 1.0 mm in width on average. — upper surface color and texture: commonly near Green Group 138B; covered in short pubescence. — under surface color and texture: commonly near Yellow-Green Group 144A; puberulent.

*Receptacle*.—Pistils stand on the bottom and wall. — color: commonly near Yellow-Green Group 144A. — diameter: approximately 4.0 mm on average. — surface texture: smooth. — shape: round.

*Peduncle*.—Length: approximately 1.8 cm on average. — diameter: approximately 1.0 mm on average. — surface texture: smooth. — color: commonly near Yellow-Green Group 144A.

*Flower*.—Diameter: approximately 3.5 cm on average. — height: approximately 1.5 cm on average. — duration: flower is on the plant approximately 7 days. — form: double. — number of petals under normal conditions: approximately 24 petals on average. — shape of the petal: overall: broadly obovate. base: cuneate. apex: rounded. — petal length: approximately 1.5 cm on average. — petal width: approximately 1.2 cm on average. — petal margin: entire. — petal drop: good. — fragrance: slight and sweet. — color when opening begins: upper petal surface: commonly near Red-Purple Group 68A and near White Group NN155A at the point of attachment; occasional central striping of near White Group NN155A is exhibited. under petal surface: commonly near Red-Purple Group 68A and near White Group NN155A at the point of attachment. — color at end of blooming: upper petal surface: commonly near Red-Purple Group 67A and near White Group NN155A at the point of attachment. under petal surface: commonly near Red-Purple Group 67B and near White Group NN155A at the point of attachment.

*Petaloids*.—Number 3 per flower, on average. — color: upper surface is commonly near Red-Purple Group 68A with central striping of near White Group NN155A, under surface is commonly near Red-Purple Group 68B with central striping of near White Group NN155A. — length: approximately 1.0 cm on average. — width: approximately 4.0 mm on average. — texture: smooth. — margins: variable, entire to erose. — shape: variable, oblong and mostly curving inward, apex is round, and base is cuneate.

*Stamen*.—Number is approximately 40 on average. — anthers: coloration is commonly near Yellow-Orange Group 22A. — filaments: length is approximately 6.0 mm on average and coloration is commonly near Yellow-Orange Group 20A.

*Pistils*.—Arrangement is separate and free; number is approximately 18 on average. — styles: length is approximately 4.0 mm on average and coloration is commonly near Yellow Group 2B. — stigmas: diameter is approximately 1.0 mm on average and coloration is commonly near Yellow Group 2A.

*Pollen*.—Color is commonly near Yellow-Orange Group 21A and a moderate amount is present.

*Hips/seeds*.—None observed.

Development:

*Vegetation*.—Medium green, semi-glossy, vigorous and strong.

*Blooming*.—Abundant and substantially continuous from spring through frost, typically from May to October in southeastern Pennsylvania.

*Resistance to disease*.—Excellent resistance to black spot, rust, and powdery mildew.

*Hardiness*.—USDA hardiness zone is 4-10.

Cytology:

*Ploidy*.—Diploid (2n=2x=14); meristematic root tip cells in the stage of metaphase of mitosis were observed to have 14 chromosomes under a light microscope at 400× magnification.

'Zlepolone' has not been observed under all possible environmental conditions to date. Accordingly, it is possible that the phenotypic expression may vary somewhat with changes in light intensity and duration, cultural practices, and other environmental conditions.

I claim:

1. A new and distinct variety of Polyantha Rose plant characterized by the following combination of characteristics:

(a) forms attractive, double deep purplish pink colored blossoms abundantly and substantially continuously, (b) exhibits a very bushy and compact growth habit, (c) forms vigorous vegetation, (d) provides attractive ornamental semi-glossy, medium green foliage, and (e) exhibits excellent disease resistance;

substantially as herein shown and described.

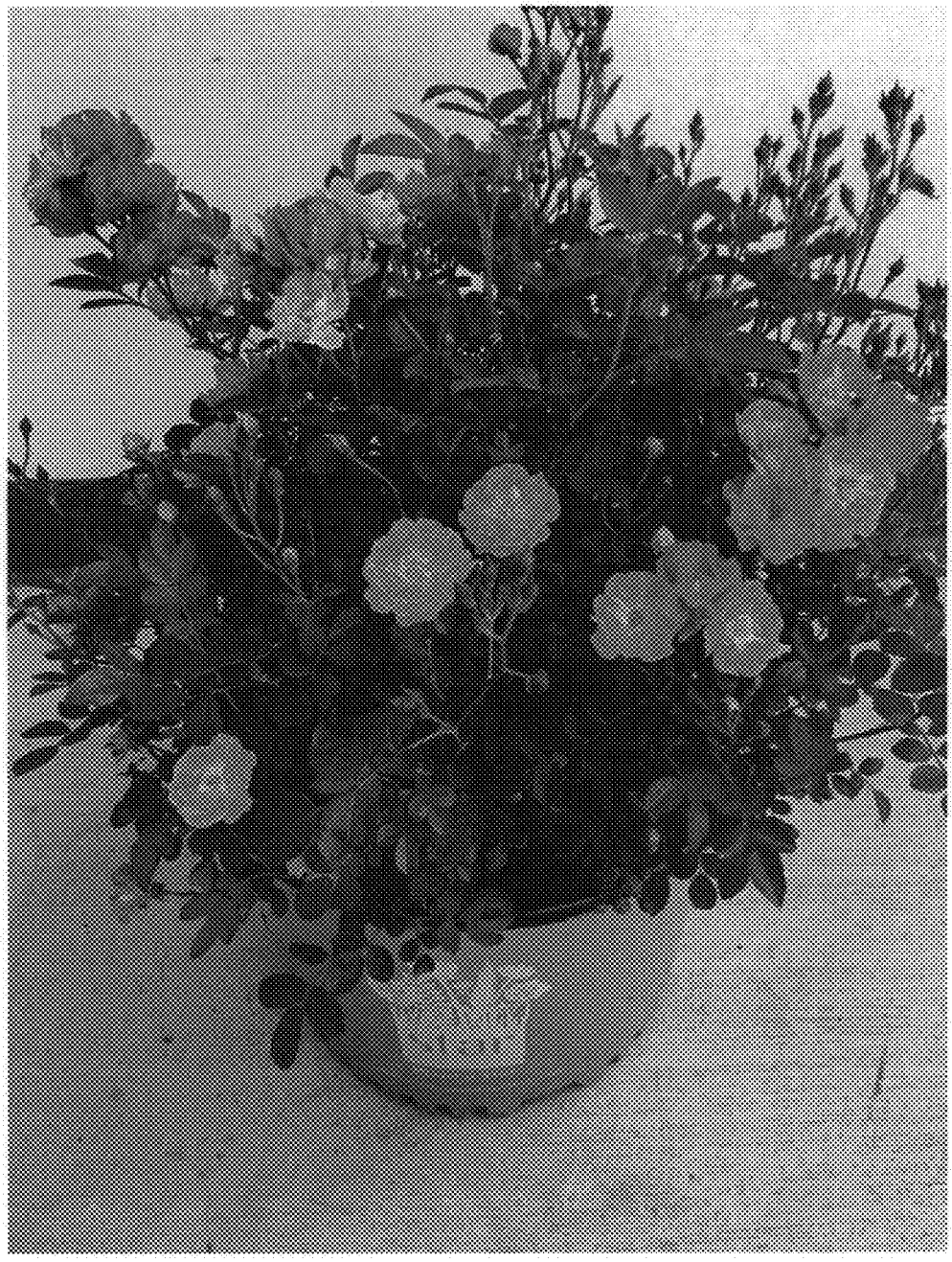

* * * * *